US00PP12183P2

(12) United States Plant Patent
Whiting

(10) Patent No.: US PP12,183 P2
(45) Date of Patent: Oct. 30, 2001

(54) *EREMOCHLOA OPHIUROIDES* GRASS PLANT 'ET-119'

(76) Inventor: Tania L. Whiting, Post Office Box 204, Wanneroo, WA 6065 (AU)

( * ) Notice: Subject to any disclaimer, the term of this patent is extended or adjusted under 35 U.S.C. 154(b) by 0 days.

(21) Appl. No.: 09/432,219

(22) Filed: Nov. 3, 1999

(30) Foreign Application Priority Data

Nov. 25, 1998 (AU) ..... 94152/98

(51) Int. Cl.[7] ..... A01H 5/00
(52) U.S. Cl. ..... Plt./388
(58) Field of Search ..... Plt./388

*Primary Examiner*—Bruce R. Campell
*Assistant Examiner*—Annette H. Para

(57) ABSTRACT

A new and distinct variety of *Eremochloa ophiuroides* grass plant 'AUS-CEN' as herein described and illustrated which is principally characterized by a moderate olive green color (color number 125 m O1 Gentlemen: of the ISCC-NBS color chart) and a more dense turfgrass surface, relative to 'ET-26'.

5 Drawing Sheets

BACKGROUND OF THE INVENTION

Figure 4:
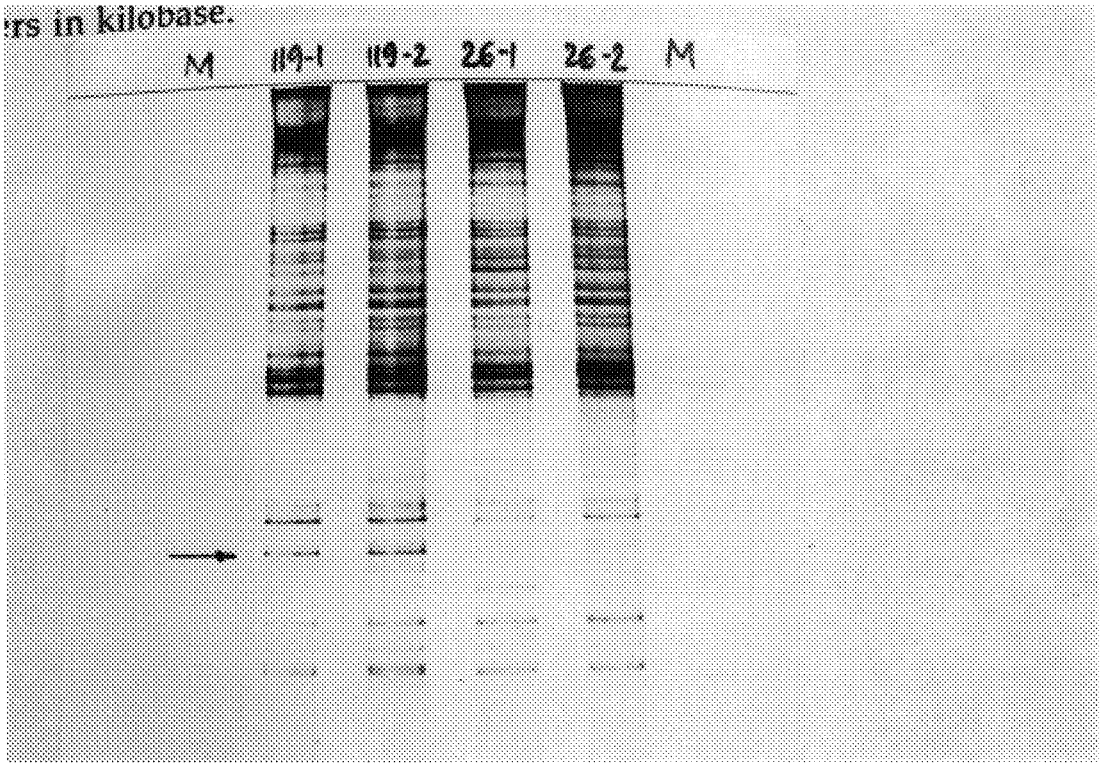

The present invention and discovery relates to a new and distinct variety of *Eremochloa ophiuroides* grass plant, which I developed through a cross-pollination of two selected varieties of *Eremochloa ophiuroides* grass plants identified as 'ET-26' and 'ET-85'. This cross-pollination was done by me at Gingin, Western Australia.

SUMMARY OF THE INVENTION

I collected seeds from this cross-pollination of 'ET-26' and 'ET-85' and planted the seeds out in germinating trays. Samples of 'ET-26' and 'ET-85' (both unpatented) are existing varieties obtainable by written application and on payment of an amount equivalent to market value to:

Mr. H. F. Whiting,

PO Box 204.

Wanneroo WA 6065.

At about three months after germinating these seeds I selected one hundred of the most rapidly growing seedlings with the best color and density characteristics relative to 'ET-26'. I broke off stolon from each selection and transplanted each selection into fifteen centimeter diameter containers. As these stolon grew and developed I once again made further selections based on improved color and density characteristics relative to 'ET-26' resulting in a final selection of seven from the original one hundred seedlings. I further asexually transplanted these seven selections into two meter by two meter plots for further evaluation. Once these seven two meter square plots became established through the spreading of the planted stolon, I formed a turfgrass surface by fertilizing, watering and mowing. The new claimed variety of *Eremochloa ophiuroides* grass plant is the final selection of those seven F1 generation selections and which I have designated 'AUS-CEN'. This new variety of *Eremochloa ophiuroides* grass plant spreads vigorously by stolon to produce a superior variety that is very dense, dark green in color with a more dense turfgrass surface when compared to the closest known variety 'ET-26'. During the continued asexual reproduction from stolon I have confirmed that the above characteristics are transmitted through succeeding propagation, and have confirmed that the new claimed variety of *Eremochloa ophiuroides* grass plant 'AUS-CEN' has the unique combination of characteristics. It is practical to repeat the invention using current state of the art techniques, to carry out the number of trials necessary to achieve the result.

The new and distinct variety of *Eremochloa ophiuroides* grass plant 'AUS-CEN' is illustrated in the accompanying photographs, with the photographs of the closest known variety of *Eremochloa ophiuroides* grass plant 'ET-26'. The most noticeable variations between the new claimed variety of *Eremochloa ophiuroides* grass plant 'AUS-CEN' and the closest known variety of *Eremochloa ophiuroides* grass plant 'ET-26 ' is that the new claimed variety has a more vigorous establishment rate with a more dense turfgrass surface with a dark green color and with unique DNA patterns.

Asexual reproduction by vegetative cuttings in Australia (Gingin, Western Australia) has established that the characteristics of the new variety are fixed and firmly established to a succeeding generation's asexual reproduction.

BRIEF DESCRIPTION OF ILLUSTRATIONS

FIG. 1. Is a photograph of the inflorescence taken from the same test area, of the new claimed variety of *Eremochloa ophiuroides* 'AUS-CEN' showing the stigmas of yellow white color, colour number 92 y White of the ISCC-NBS centroid colour chart; with the newly formed anthers before dehiscence of greyish reddish purple colour, colour number 245 gy r P of the ISCC-NBS centroid colour chart.

FIG. 2. Is a photograph of the inflorescence taken from the same test area, the inflorescence in the photograph is of the closest known variety of *Eremochloa ophiuroides* 'ET-26' showing the stigmas of pale yellowish pink color, color number 31 p y Pink of the ISCC-NBS centroid color chart; with the newly formed anthers before dehiscence of deep reddish purple color, color number 238 deep r P of the ISCC-NBS centroid color chart.

FIG. 3. Is a photograph of two stolon taken from the same test area, this photograph shows the stolon on the top in the photograph of the closed known variety of *Eremochloa ophiuroides* 'ET-26' with internode spacings closer together and of a dark olive green color number 126 d O1 Gentlemen: of the ISCC-NBS centroid color chart; when compared to the stolon in the bottom of the photograph which is the new claimed variety of *Eremochloa ophiuroides* grass plant 'AUS-CEN' which has internode spacings further aprat and of a moderate olive green, color number 125 m O1 Gentlemen: of the ISCC-NBS centroid color chart.

FIG. 4. This photograph shows the unique DNA patterns of the new claimed variety of *Eremochloa ophiuroides* grass plant 'AUS-CEN'.

Figure 5:
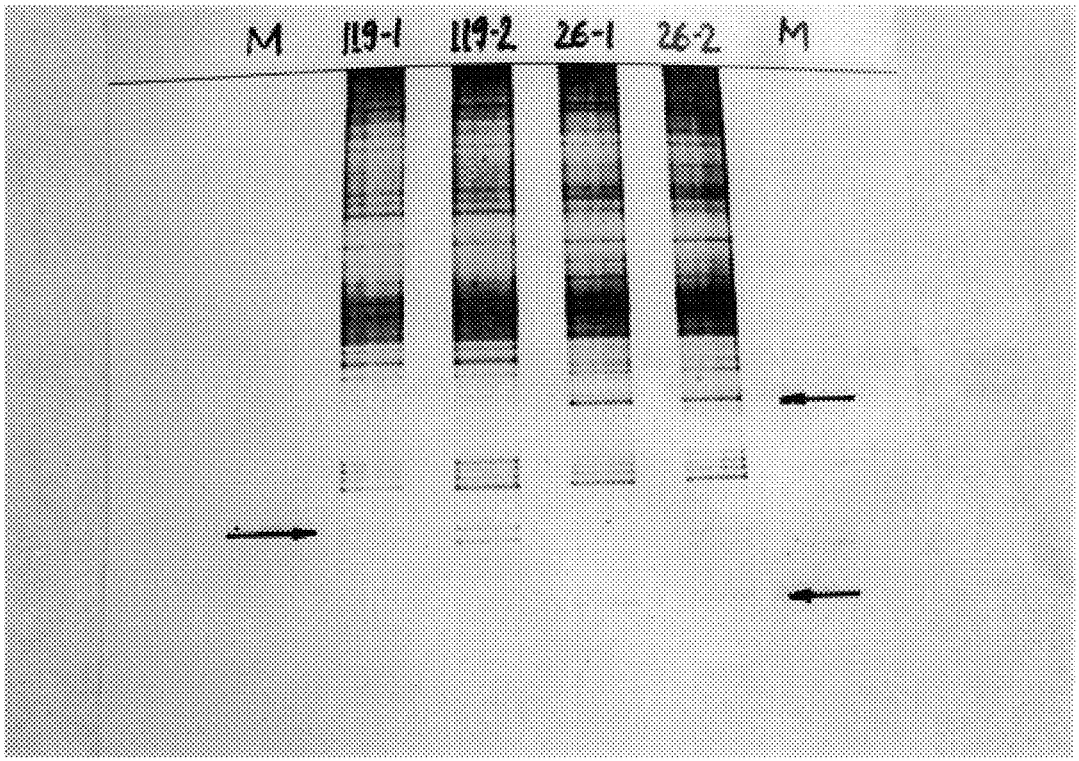

FIG. 5. This photograph shows the unique DNA patterns of the closest known variety of *Eremochloa ophiuroides* grass plant 'ET-26'.

DESCRIPTION OF THE NEW VARIETY

A detailed description of the new and distinct variety of *Eremochloa ophiuroides* grass plant 'AUS-CEN' is:

(a) Plants are mature 1½ year old and grown in unfertilzed container environment. The color described is the general overall color of the plant including the whole leaf area where appropriate. is:
(b) An attractive moderate olive green colour, colour number 125m O1 Gentlemen: of the ISCC-NBS centroid colour chart.
(c) The grass is low growing, with an upright erect growth characteristic.
(d) The grass spreads by above ground stolon, forming a more dense uniform textured surface with an extensive root system; stolon internode spacings are 3–4 centimeters apart.
(e) Culms vary in height 11–17 centimeters.
(f) Leaves folded in bud shoot.
(g) The leaf blade is flat and keeled 1.5–2 centimeters in width and 8–10 centimeters long.
(h) The first mature leaf is 6–8 centimeters long.
(i) The leaf blade is sparsely hairy near the base and also the margins.
(j) The ligule is a short purplish (219 deep P of the ISCC-NBS centroid colour chart membrane, with a ciliate fringe.
(k) Auricles are absent.
(l) The collar is broad, continuous, constricted by a fused keel pubescent, tufted at lower edge.
(m) The sheath is very compressed, glabrous with several hairs at the top 1.5 millimeters long.
(n) The entire plant is glabrous exept at the base of the leaf blade and at the top of the sheath where several hairs are present. The leaf blade is sparsely hairy near the base and also along the margins for about 15 to 20 mm.
(o) The inflorescence consists of a single spike of the stem.
(p) The spike contains stigmas of yellow white color, colour number 92 y White of the ISCC-NBS centroid colour chart; the newly formed anthers before dehiscence of grayish reddish purple colour, colour number 245 gy r P of the ISCC-NBS centroid colour chart.
(q) Seed information: color of seed is 56 deep br of the ISCC-NBS centroid colour chart; seeds are about 2 mm. length, about 1 mm. width and about 0.5 mm. depth. From planting, germination occurs about 8 to 12 days.

A detailed description of the closest known variety of *Eremochloa ophiuroides* grass plant 'ET-26' is:

(a) An attractive dark olive green colour, colour number 126 d O1 Gentlemen: of the ISCC-NBS centroid colour chart.
(b) The grass is low growing, with an upright erect growth characteristic.
(c) The grass spreads by aboveground stolon, forming a more dense uniform textured surface with an extensive root system; stolon internode spacings are 2–2.5 centimeters apart.
(d) Culms vary in height 9–14 centimeters.
(e) Leaves folded in bud shoot.
(f) The leaf blade is flat and keeled 1–1.5 centimeters in width and 8–10 centimeters long.
(g) The first mature leaf is 4–6 centimeters long.
(h) The leaf blade is sparsely hairy near th base and also the margins.
(i) The ligule is a short purplish membrane, with a ciliate fringe.
(j) Auricles are absent.
(k) The collar is broad, continuous, constricted by a fused keel pubescent, tufted at lower edge.
(l) The sheath is very compressed, glabrous with several hairs at the top 1.5 millimeters long.
(m) The entire plant is glabrous except at the base of the leaf blade and at the top of the sheath where several hairs are present.
(n) The inflorescence consists of a single spike of the stem.
(o) The spike contains stigmas of pale yellowish pink color, colour number 31 p y Pink of the ISCC-NBS centroid colour chart; the newly formed anthers before dehiscence of deep reddish purple colour, colour number 238 deep r P of the ISCC-NBS centroid colour chart.

DNA Amplification Fingerprinting Analysis of Two Centipedegrass Samples

Genomic DNA was isolated from freshly grown material—several young blades of grass were ground in liquid nitrogren and DNA extracted using a modification of the method developed by (Dellaporta et al (1083). Plant Molecular Biology Reporter 1:19–21).

DNA was quantified by flourimetry and then diluated and amplified using the standard high primer-low template DNA ratio according to an established protocol of DNA amplification fingerprinting [Caetano-Anollé, et al (1991) DNA amplification fingerprinting using single short arbitrary oligonulceotide primers Bio Technology 9:553–557].

Stoffel fragment of Taq DNA polymerase from Perkin Elmer Corp. was used to amplify gnomic DNA. Primers 8.6i 5'GTTACGCC3' and B10 5'CTGCTGGAC3' were used. Amplification occurred in an MJR PT200 thermocycler, using the optimized DAF amplification program DAF15 [Caetano-Anollé, et al (1991 ) DNA amplification fingergerprinting using single short arbitrary oligonulceotide primers Bio Technology 9:553–557]. This involves fast ramping, high annealing temperature (55° C.) , and an extension step at 72° C. Resulting amplication products were resolved using "SUPERGEL" polyacramide gel electrophoresis (Bassam and Bentely, 1995, Biotechniques 19, 568–573) and an established silver staining procedure [Bassam et al (1991) A rapid and sensitive silver staining of nucleic acids in polyacrylamide gels Anal. Biochemistry 196:80–83]. Duplicate amplifications were run and shown on gels.

The DNA fingersprints are set out in FIGS. 4 and 5. About 15 major amplification products, seen as strong bands, and about 30 minor ones are seen. All replications are identical supporting the repeatability of the method. The lanes on the sides represent molecular size markers used to determine the size (in base pairs; A:T or G:C) of the amplification products (1000 base pairs [bp], then 700 bp, 500 bp (a doublet), 400 bp, 300 bp, 200 bp and 100 bp).

I claim:

1. A new plant of *Eremochloa ophiuroides* grass plant named 'AUS-CEN' as herein described and illustrated which is principally characterized by a moderate olive green color (color number 125 m O1 G of the ISCC-NBS color chart) and a more dense turfgrass surface, relative to 'ET-26'.

* * * * *